(12) United States Patent  
Duncan et al.

(10) Patent No.: US 10,737,112 B2  
(45) Date of Patent: Aug. 11, 2020

(54) WATER-FILTERED NEAR INFRARED SAUNA

(71) Applicants: Raleigh Duncan, Berkeley, CA (US); Andrew Kaps, Sausalito, CA (US)

(72) Inventors: Raleigh Duncan, Berkeley, CA (US); Andrew Kaps, Sausalito, CA (US)

(73) Assignee: Sauna Works Inc., Berkeley, CA (US)

( * ) Notice: Subject to any disclaimer, the term of this patent is extended or adjusted under 35 U.S.C. 154(b) by 0 days.

(21) Appl. No.: 15/153,721

(22) Filed: May 12, 2016

(65) Prior Publication Data

US 2017/0326384 A1 Nov. 16, 2017

Related U.S. Application Data

(60) Provisional application No. 62/161,245, filed on May 13, 2015.

(51) Int. Cl.
*A61H 33/06* (2006.01)
*A61N 5/06* (2006.01)

(52) U.S. Cl.
CPC ......... *A61N 5/0625* (2013.01); *A61H 33/063* (2013.01); *A61H 2033/061* (2013.01); *A61N 2005/0636* (2013.01); *A61N 2005/0659* (2013.01); *A61N 2005/0667* (2013.01); *A61N 2005/0668* (2013.01)

(58) Field of Classification Search
CPC ............ A61H 33/063; A61H 2033/061; A61N 5/0625; A61N 2005/0636; A61N 2005/0659; A61N 2005/0667; A61N 2005/0668

See application file for complete search history.

(56) References Cited

U.S. PATENT DOCUMENTS

| | | | | |
|---|---|---|---|---|
| 4,641,227 | A * | 2/1987 | Kusuhara | F21S 8/006 362/1 |
| 8,915,948 | B2 * | 12/2014 | Altshuler | A61B 5/6843 128/898 |
| 2006/0052847 | A1 * | 3/2006 | Davenport | A61B 18/203 607/88 |
| 2007/0154505 | A1 * | 7/2007 | Manico | A01N 59/16 424/405 |
| 2014/0215708 | A1 * | 8/2014 | Benda | A61H 33/063 4/524 |

\* cited by examiner

*Primary Examiner* — Janie M Loeppke
(74) *Attorney, Agent, or Firm* — Kwan & Olynick LLP

(57) ABSTRACT

A heating element for a sauna comprising an infrared heating element and a water filter for filtering out the far and mid infrared frequencies.

9 Claims, 3 Drawing Sheets

WATER-FILTERED NEAR INFRARED SAUNA

CROSS-REFERENCE TO RELATED APPLICATIONS

The present application takes priority from Provisional App. No. 62/161,245, filed May 13, 2015, which is incorporated herein by reference.

BACKGROUND

Infrared light emitters are frequently used in saunas to provide therapeutic heat to the body without heating the sauna room. This is an efficient way to deliver heat to the body for any therapeutic purpose such as relieving joint pain, improving circulation, and encouraging sweating.

The three categories of infrared light are far infrared, mid infrared, and near infrared. Typically, near-infrared is classified as a wavelength range of 0.7-5 microns, mid-infrared as a wavelength range of 5 to 40 microns, and far infrared as a wavelength range of 40 to 350 microns. These categories have different effects on the human body.

Generally, the longer the wavelength, the less deeply the infrared radiation penetrates into the human body. Therefore, far infrared radiation is good at heating the skin and tissues close to the skin, while near infrared radiation can penetrate more deeply into the human body and reach deeper tissues.

Oftentimes, a need exists for substantial quantities of heat to be delivered deeply into the human body. For example, a patient undergoing hyperthermia treatment may need to raise their core temperature quickly. However, a standard infrared heating element emits near, mid, and far infrared light, and if enough near infrared is delivered to the patient for therapeutic purposes, the far infrared that the heating element also delivers could burn the patient's skin.

It is known that far and mid infrared light is absorbed by water. Water filtering is used in a clinical setting for infrared heating elements used in a hospital setting to filter out the far and mid infrared light and leave only the near infrared light. While this can be useful in a hospital, it is desirable to achieve the same effects in a sauna.

A need exists for a sauna heating element that provides only near infrared light.

LIST OF FIGURES

Figure 1:
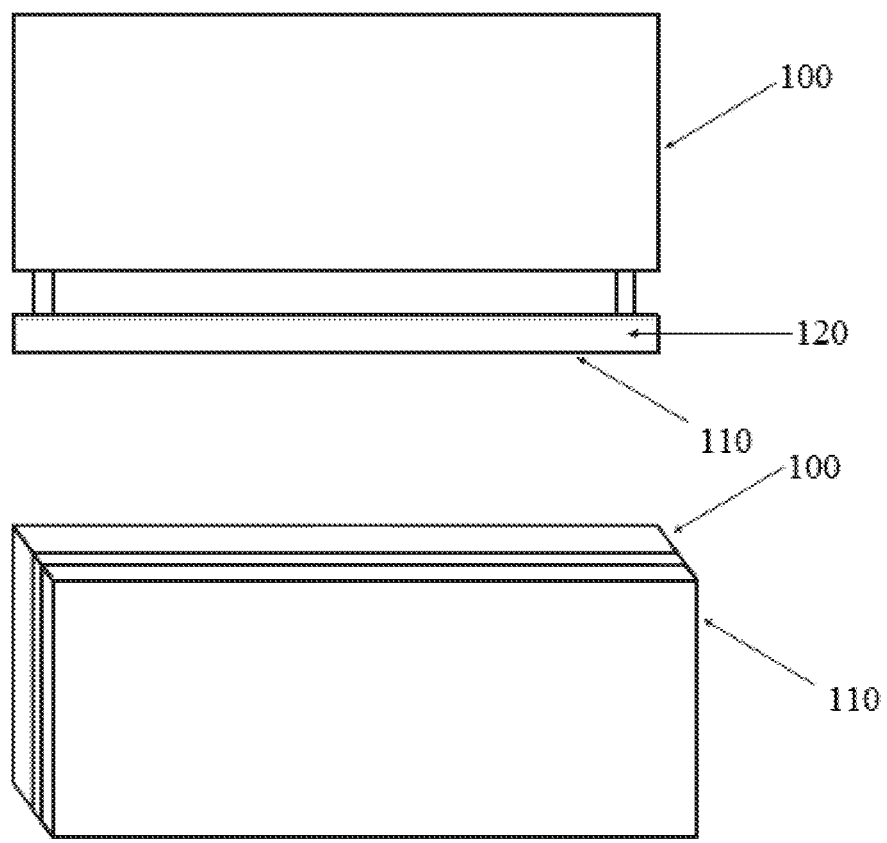
Figure 2:
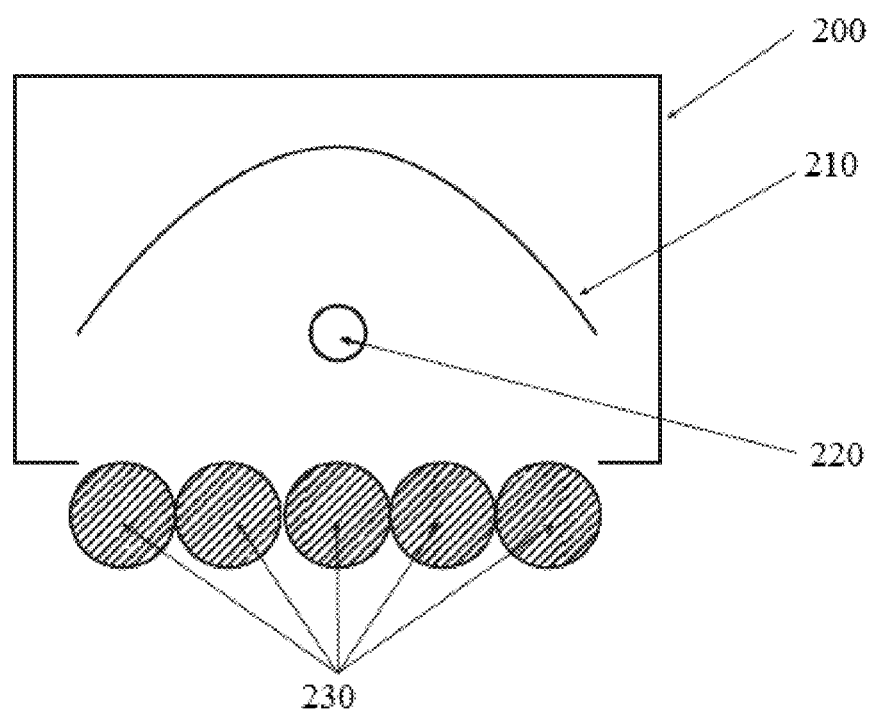
Figure 3:
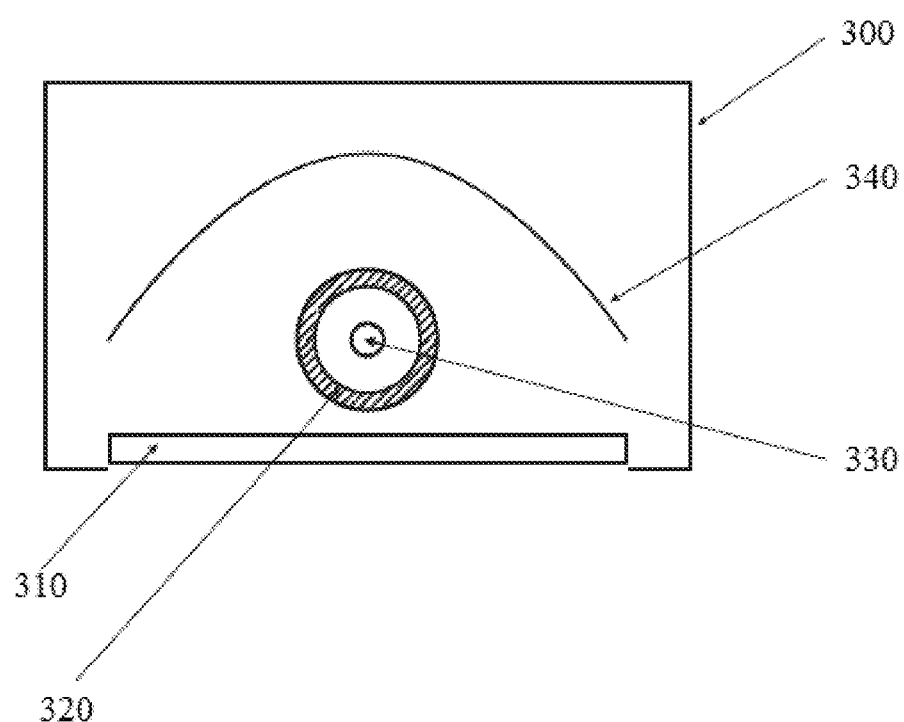

FIG. 1 shows an embodiment of the present invention.
FIG. 2 shows another embodiment of the present invention.
FIG. 3 shows another embodiment of the present invention.

SUMMARY OF THE INVENTION

An object of the present invention is to provide a sauna that only delivers near infrared light to the user.

Another object of the present invention is to provide a sauna with heaters that do not burn a user's skin while in use.

Another object of the present invention is to provide a sauna with heaters that use water to filter out far and mid infrared light.

The present invention comprises a sauna with one or more heaters aimed at the interior of the sauna. Each of the heaters comprises a heating element which emits at least one wavelength of infrared light, and a water filtering element comprising a water container and water, shaped and placed in such a way that the infrared light passes through the water before reaching the interior of the sauna.

The thickness of the water layer is preferably at least 0.25".

In an embodiment, the water container is a parallelepiped with a thickness of at least 0.25". In another embodiment, the water container comprises a plurality of tubes arranged in a plane, wherein the tubes are at least 0.25" in diameter. In another embodiment, the heater has a linear shape and the water container comprises a hollow cylinder where the heater is at the axis of the hollow cylinder. The thickness of the hollow cylinder is preferably at least 0.25".

The heater may be a planar heater, a linear heater, or any other heater shape or configuration. The heater may also comprise a parabolic reflector to reflect some of the infrared radiation towards the interior of the sauna.

Since the water in the water container tends to heat up, an embodiment of the present invention comprises a pump for recirculating the water and a cooling element for cooling the water. In another embodiment, the water may comprise an antibacterial additive.

The water container is preferably made of glass.

DETAILED DESCRIPTION OF THE PREFERRED EMBODIMENT

In the preferred embodiment, the present invention comprises a sauna comprising at least one heater. Each heater comprises an infrared heating element for use in a sauna and a water filter that filters out the far and mid infrared light from the heating element. The water filter preferably comprises at least 0.25" of water for proper filtering, but may contain less than that depending on user requirements.

The sauna can be of any size or configuration, ranging from a large multi-person sauna chamber to a small one-person sauna chamber. The heaters may be mounted on the walls of the sauna, on the floor of the sauna, or anywhere else on the interior of the sauna.

FIG. 1 shows one embodiment of the heater of the present invention (two views). The heater 100 preferably provides a full spectrum of infrared light; however, any infrared heater with a planar configuration could be used for this purpose. A container 110 of water 120 is located in front of the heater as shown in the Figure. The water container 110 is preferably at least 0.25" thick to provide appropriate filtering, but may be any thickness. The water container 110 is preferably located close to the heater 100, so that almost all of the infrared light emitted by the heater 100 is filtered by the water 120. In the embodiment shown in the Figure, the water container 110 is a parallelepiped.

The water container 110 is preferably made of glass to improve transmission of near-infrared light, but other materials that transmit near-infrared light are also permissible. For example, the water container 110 may also be made of transparent plastic such as polycarbonate.

FIG. 2 shows another embodiment of the invention. Here, the heating element 220 is a halogen tube. A reflector 210 directs the infrared radiation in the direction of the interior of the sauna. Several glass tubes 230 are placed in front of the reflector 210 as shown in the Figure, with no gaps between the tubes. The tubes are at least 0.25" in diameter, made of borosilicate glass, and filled with water. The water preferably circulates to prevent overheating. The heater is preferably contained in a case 200 for easy installation in the sauna. In this embodiment, as shown, the case 200 and the tubes 230 are placed so that no unfiltered infrared radiation can reach the sauna interior.

It will be understood that the glass tubes 230 could also be placed in front of a planar heater or any other heater configuration. The combination shown in the Figure is simply an exemplary embodiment and is not meant to restrict the invention to this particular combination.

FIG. 3 shows another embodiment of the heater of the present invention. In this embodiment, the heating element 330 is a halogen tube or another heater with a linear configuration. Two concentric glass tubes 320 are placed around the heating element as shown, and the gap between the two concentric glass tubes is filled with water. A reflector 340 directs the infrared radiation in the direction of the sauna user, and a glass cover 310 and a metal case 300 are used to enclose the heating element for aesthetics and safety. The gap between the two concentric glass tubes 320 is preferably at least 0.25" to provide adequate filtering, and the water preferably circulates to prevent overheating. This embodiment offers the advantage that, unlike in the prior-discussed embodiments, there is no way for any unfiltered infrared radiation to escape.

It will be understood that multiple other configurations are possible with the present invention, as long as there is (a) a heater emitting infrared light and (b) a container comprising water, located between the heater and the interior of the sauna.

Any type of heating element may be used with the present invention. In the preferred embodiment, the heating element is a halogen tube, as they are commonly used in infrared saunas, but any other infrared heating element may be used as long as it generates sufficient amounts of near infrared radiation for therapeutic purposes.

In an embodiment, the water in the water container circulates, to prevent overheating of the water. The water may also be cooled as it circulates. This is preferably done with a pump and a cooling element.

Additives may be added to the water to improve its filtering ability or to prevent bacterial or algae growth. If the water circulates, it may be circulating at any flow rate that is sufficient to prevent overheating.

Any other shape of water filter may also be used, as long as it provides a layer of water between the heater and interior of the sauna that is at least 0.25" thick. The three embodiments shown in the Figures are solely shown as example embodiments and are not meant to be limiting.

In an embodiment, a cooling element may be added to the water circulation system to prevent the water from overheating.

While in the preferred embodiment, the water filter is rigidly attached to the heater, it may also be attached to the wall of the sauna in front of the heater. The means of attachment is preferably mounting brackets, but could be any other attachment method that results in rigid attachment.

While example embodiments are described in this disclosure, it will be apparent to a person of reasonable skill in the art that other embodiments are also possible. The present disclosure is not intended to be limited to just the three embodiments described above; the only limitations to the invention are found in the appended claims.

What is claimed is:

1. A system comprising:
   at least one heater configured to be mounted on a wall of a sauna, wherein the at least one heater comprises:
   a heating element, said heating element being configured to generate heat for the sauna, and being configured to generate and emit near infrared radiation, mid infrared radiation, and far infrared radiation, said heating element emitting such infrared radiation towards an interior of the sauna, said heating element being contained in a case configured to be mounted in a sauna;
   a water filtering element, comprising a water container and water, said container being made of glass, and said water filtering element being located and configured such that the infrared radiation passes through the water before entering the interior of the sauna, wherein the water filtering element further comprises two concentric glass tubes comprising an inner glass tube and an outer glass tube, wherein a space between the two concentric glass tubes is filled with water, and wherein the heating element is positioned within a cavity defined by an inner radius of the inner glass tube.

2. The system of claim 1, wherein the water filtering element comprises a thickness, wherein the thickness of the water filtering element is at least 0.25".

3. The system of claim 1, wherein the water container is shaped like a parallelepiped with a length, a width, and a thickness, wherein the thickness of the parallelepiped is at least 0.25".

4. The system of claim 1, wherein the water container comprises a plurality of tubular elements, the tubular elements disposed parallel to each other and parallel to the heating element in a plane parallel to the heating element, wherein the diameter of each tubular element is at least 0.25".

5. The system of claim 4, wherein the tubular elements are in contact with each other.

6. The system of claim 1, wherein the heating element has a linear shape and the water container is shaped like a hollow cylinder with the heating element at an axis of symmetry of the cylinder, wherein the thickness of the water container is at least 0.25".

7. The system of claim 1, wherein the heating element comprises a parabolic reflector that reflects the infrared radiation towards the interior of the sauna.

8. The system of claim 1, wherein the water comprises an antibacterial additive.

9. The system of claim 1, wherein at least one water filtering element is rigidly attached to at least one heating element.

* * * * *